United States Patent
Manganini et al.

[11] Patent Number: 5,876,380
[45] Date of Patent: Mar. 2, 1999

[54] PORTABLE SYRINGE DISPENSER SYSTEM

[76] Inventors: Steven J. Manganini, 105 Braeside Rd., Falmouth, Mass. 62540; Kenneth W. Doherty, 87 Blacksmith Shop Rd., W. Falmouth, Mass. 02576

[21] Appl. No.: 665,619

[22] Filed: Jun. 18, 1996

Related U.S. Application Data

[63] Continuation-in-part of Ser. No. 325,604, Oct. 19, 1994, abandoned.

[51] Int. Cl.⁶ ................................................. A61M 5/00
[52] U.S. Cl. ........................... 604/191; 604/88; 604/205
[58] Field of Search ........................ 604/207–211, 87, 604/88, 89, 90, 91, 62, 63, 131, 132, 135, 136, 155, 201, 202, 205, 191; 128/DIG. 1, DIG. 26; 222/45, 46, 48, 145.1, 136, 330, 163

[56] References Cited

U.S. PATENT DOCUMENTS

| | | | |
|---|---|---|---|
| 4,040,420 | 8/1977 | Speer | 604/191 X |
| 4,416,663 | 11/1983 | Hall | 604/163 |
| 4,857,056 | 8/1989 | Talonn | 604/135 |
| 5,115,816 | 5/1992 | Lee | 128/749 |
| 5,199,949 | 4/1993 | Haber et al. | 604/88 |
| 5,290,259 | 3/1994 | Fischer | 604/218 |
| 5,536,249 | 7/1996 | Castellano et al. | 604/65 |
| 5,593,390 | 1/1997 | Castellano et al. | 604/187 |
| 5,611,784 | 3/1997 | Barresi et al. | 604/211 |
| 5,628,309 | 5/1997 | Brown | 128/632 |
| 5,651,775 | 7/1997 | Walker et al. | 604/207 |

FOREIGN PATENT DOCUMENTS 0245816 5/1987 Germany ............................ 604/191

*Primary Examiner*—Wynn Wood Coggins
*Assistant Examiner*—Deborah Blyveis
*Attorney, Agent, or Firm*—Carla Magda Krivak

[57] ABSTRACT

A portable syringe dispenser system capable of holding one or more syringes containing different types of fluid medicine therein. Filled syringes, holding enough fluid medicine for multiple injections, are placed into syringe holders in the dispenser and inserted into a sterile mixing chamber. The dosage of each type of fluid medicine in each syringe is independently adjusted employing a dose adjusting indicator system. An activation system allows all doses of the fluid medicine to be simultaneously injected through a replaceable sterile needle. The sterile needle can remain on the dispenser system. The sterile needle maintains its sterility by sealing it with a sealing cap. This allows the needle to be reused. In addition, a dosage/time recording unit can be attached to the portable syringe dispensing system to accurately record at least the time, date and amount of fluid medicine injected. A plurality of these recordings can be made.

19 Claims, 8 Drawing Sheets

3,876,380

PORTABLE SYRINGE DISPENSER SYSTEM

This is a continuation-in-part of application Ser. No. 08/325,604, filed on Oct. 19, 1994, now abandoned.

BACKGROUND OF THE INVENTION

1. Field of the Invention

The present invention relates to a syringe dispenser capable of holding one or more syringes having different types of fluid medicine therein. More particularly, the present invention relates to a compact portable syringe dispenser system which simultaneously injects multiple medicines of varying doses. In addition, the present invention provides a dosage/time recording system to record and store in a memory at least the time, date and amount of medicine injected.

2. Description of the Related Art

Conventional insulin delivery systems include systems which require filling a syringe with insulin or a mixture of insulin prior to injection. For example, a Novolin® Pen-Needle® manufactured by Novo Nordisk A/S, allows multiple injections with one type of insulin. This product is available in prefilled disposable form. The needle can be removed after the injection and a new sterile needle can be screwed on for a next injection. This device holds 1.5 mm of a single type of insulin so that many injections can be administered, lasting up to several days. The Novolin® PenNeedle® however is restricted. Novolin® insulin must be used and comes only in cartridges of regular (hereinafter referred to as R) which is a fast-acting type of insulin, NPH (hereinafter referred to as N) which is a slower acting type of insulin, or premixed 70% N and 30% R. The cartridges are made specifically for the Novolin® PenNeedle®. Only one cartridge can be used in one pen at any one time. For a person requiring multiple injections, the type of insulin required must be those offered by Novolin® and if different insulins are required numerous Novolin® PenNeedles® must be carried.

Most insulin companies produce a premixed insulin of 70% N and 30% R. This is the most commonly used insulin mixture. This eliminates some of the cumbersome mixing procedures. The insulins are sold in 10 ml bottles that have a rubber septum on the top so that a needle can penetrate and withdraw the insulin with little risk of contamination to the insulin. The strength of the insulin is commonly u100 and at this strength, an insulin measurement of 100 units equals 1.0 ml. An insulin dependent patient usually requires one quarter unit of insulin for every pound of body weight. Therefore, for example, a person of 150 pounds requires approximately 38 units of insulin per day. Research today has proven that multiple injections that mimic the natural release of insulin within the body is the best therapy. Multiple insulin injections of either R, N or a mixture of different types of insulin throughout the day is necessary. Convenience and inconspicuousness are essential for this type of therapy since injections may have to be administered in every day places such as the work place, airplanes, buses, etc. If existing hardware is used, then a diabetic requiring multiple injections of different types of insulin may find it cumbersome. For example, if the Novolin® PenNeedle® is used, one would have to carry numerous devices to fulfill the requirements of the different types of insulin. If conventional syringe techniques are used the user must find a quiet place, such as a restroom, to draw the insulin since it is socially unacceptable to draw a syringe in public.

Other systems employ multiple cartridges containing different types of liquid medicine, such as insulin. Depressing a cartridge, using various known techniques, causes the insulin to flow into a separate mixing chamber. The quantity of each mixture in the mixing chamber is dependent on the level of depression of the cartridge. However, the prior art conventional systems require excessive time for filling syringes and an excess amount of hardware.

As an example, a procedure for an insulin injection is as follows. A syringe is filled with a recommended dosage of insulin by injecting a needle into a bottle of insulin. The amount of air injected into the insulin bottle is equivalent to the amount of insulin being extracted. This maintains pressure inside the bottle. For example, if a person requires 5 units of R insulin and 7 units of N insulin the procedure is as follows. A sterile syringe including a needle is unwrapped. The plunger on the syringe is then pulled back to, for example a 7 unit mark (the markings are on the side of the syringe). The needle is then inserted into the N insulin bottle. 7 units of air are injected into the N insulin bottle and 5 units of air are injected into the R insulin bottle. Then 7 units of insulin are extracted from the N insulin bottle. The needle is then withdrawn from the N insulin bottle. The needle is then inserted into the R insulin bottle. If 5 units of R insulin are required then the plunger on the sterile syringe is pulled back to the 12 unit mark. The needle is then withdrawn from the R insulin bottle and a dose is ready to be injected. Drawing multiple injections 4 or 5 times a day is very time consuming and awkward. Needles and public injections are publicly unacceptable so that a private place must be found to draw and inject the dose. The prior art systems are large, cumbersome and do not allow various unconventional mixtures of liquid medicines to be premeasured and simultaneously injected.

SUMMARY OF THE INVENTION

It is an object of the present invention to provide a syringe dispenser system capable of holding two or more syringes containing different types of fluid medicine, for example, different types of insulin.

It is another object of the present invention to provide a syringe dispenser system in which the system is user friendly, compact and portable, and syringes are easily inserted into the dispenser system.

It is yet another object of the present invention to provide a syringe dispenser system in which different types of liquid medicine are provided in separate syringe reservoirs and the dose of each syringe is individually adjusted.

It is still another object of the present invention to provide a syringe dispenser system in which the fluid medicines in the syringes are simultaneously injected.

It is a further object of the present invention to provide a syringe dispenser system in which the syringe reservoirs hold enough for multiple injections and the needles and fluids in the system remain sterile.

It is still a further object of the present invention to provide a syringe dispenser system which includes a dosage/time recording system for storing in memory at least the time, date and amount of medicine(s) injected.

The above-metioned features and advantages are obtained by providing a syringe dispenser system including a housing having a plurality of syringe holders, a plurality of dose adjustable syringes that are insertable into the plurality of syringe holders, the dose adjustable syringes including fluid medicine therein and being capable of several sequential dose injections, and plungers contacting each of the syringes. The dose adjustable syringes include adjusting means for each of the syringes to adjust the dosage in each syringe. The adjusting means include an indicator on each syringe, an indicator bar and adjusting screw, a threaded rod and an activation bar. Further, calibration means, syringe holding and guiding system, dose adjusting indicator system and activation system are provided.

The system of the present invention allows for fluid medicine in each of the syringes to be released and injected simultaneously. A sterile system is provided such that not only can multiple injections be administered, but they can be administered using the same needle without fear of contamination.

Further, the present invention provides a dosage/time recording system which records and stores in a memory at least the time, date and amount of fluid medicine injected. This information, along with any other pertinent information can be downloaded into available software for processing or can be sent directly, via telephone lines or otherwise, directly to a physician where an instant evaluation can occur.

These and other objects of the present invention will become apparent and more readily appreciated from the following description of the preferred embodiments, taken in conjunction with the accompanying drawings.

DESCRIPTION OF THE PREFERRED EMBODIMENTS

Figure 1A:
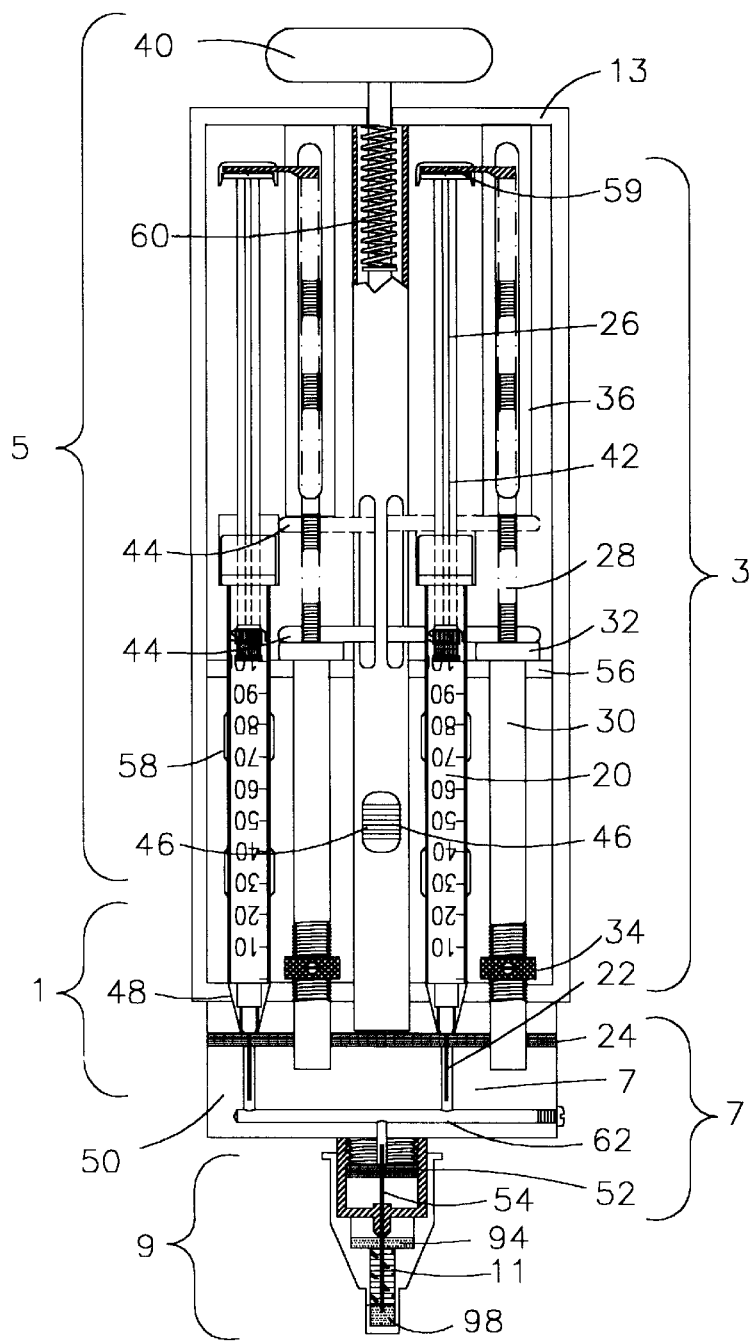
FIG. 1A is a front view of a syringe dispenser system according to a first embodiment of the present invention.
Figure 1B:
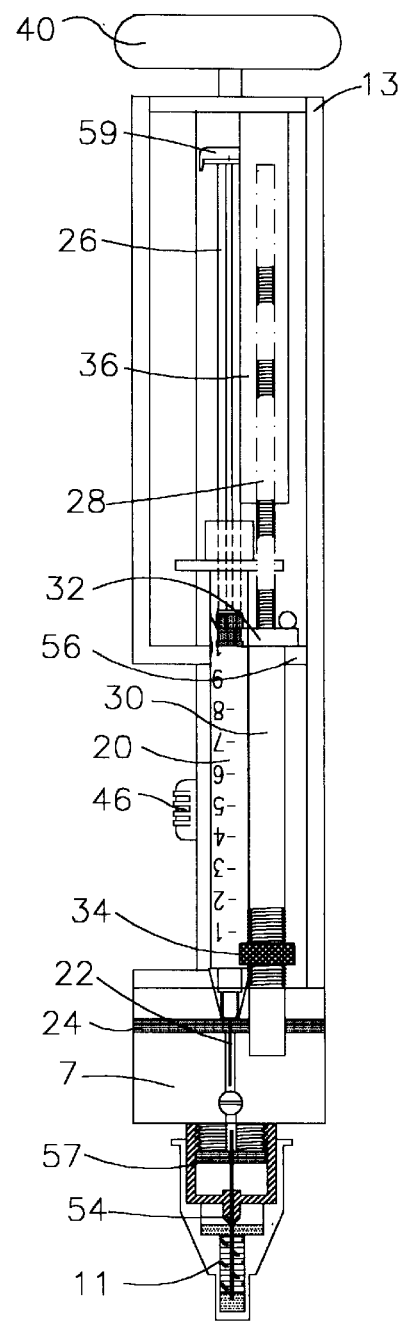
FIG. 1B is a side view of the syringe dispenser system according to the first embodiment of the present invention.

Reference will now be made in detail to the present preferred embodiments of the invention, examples of which are illustrated in the accompanying drawings. Like numerals refer to like parts throughout.

The syringe dispenser system generally includes, as shown in FIGS. 1A, 1B, 2A and 2B, a syringe holding and guiding system 1, a dose adjusting indicator system 3, an activation system 5, a sterile mixing chamber manifold 7, an injecting system 9, a sterile sealing cap 11 and a protective support structure 11.

The syringe holding and guiding system 1 holds a syringe reservoir 20 in place, guides a syringe needle 22 through a first sterile septum 24 into the sterile mixing chamber 7 and connects a syringe plunger 26 to a threaded rod 28.

The dose adjusting indicator system 3 includes a threaded tube 30 (internally threaded) having a threaded tube shoulder 32 on an upper end and an indicator dial 34 secured by a zero set screw on a lower end. The threaded rod 28 is screwed into the threaded tube 30. The threaded rod 28 is held in place by a threaded rod guide 36. An upper end of the threaded rod 28 is connected to the syringe plunger 26 by a syringe plunger holder 59.

Figure 2A:
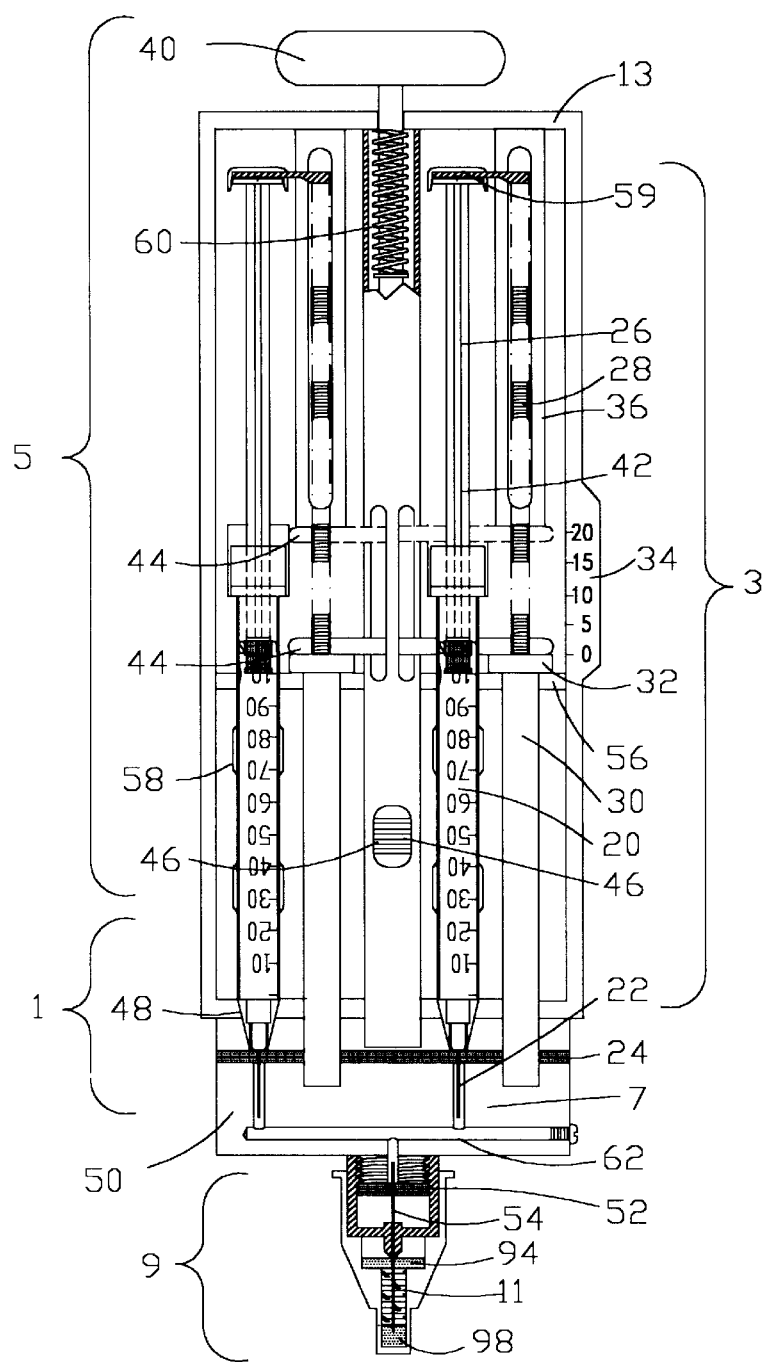
FIG. 2A is a front view of a syringe dispenser system according to a second embodiment of the present invention.
Figure 2B:
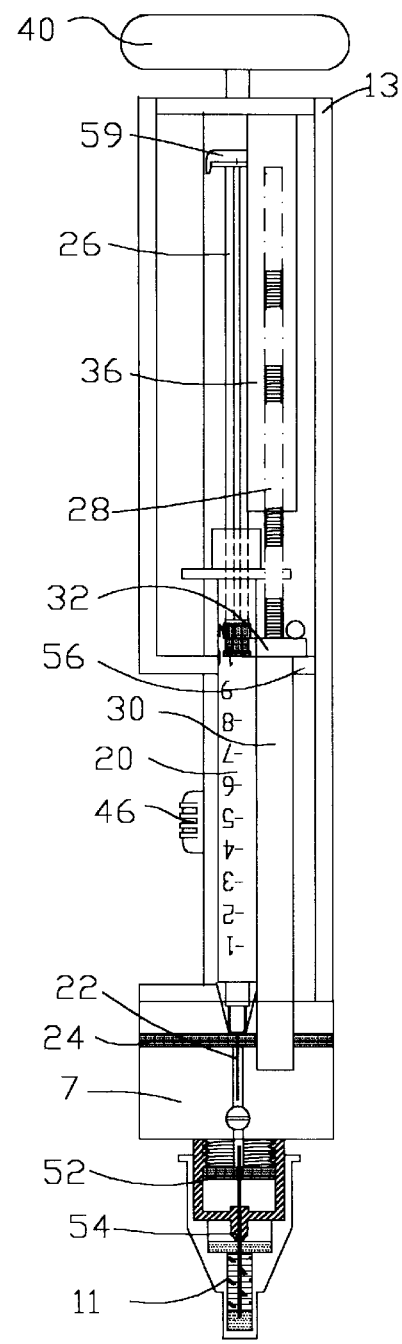
FIG. 2B is a side view of the syringe dispenser system according to the second embodiment of the present invention.

The activation system 5 can include an arming knob 40, a syringe 42 an activation bar 44 and an activation button 46, as shown in FIGS. 1A and 2A. A spring-type activation system or a battery-type activation system can also be employed and will be described herein below.

Figure 6:
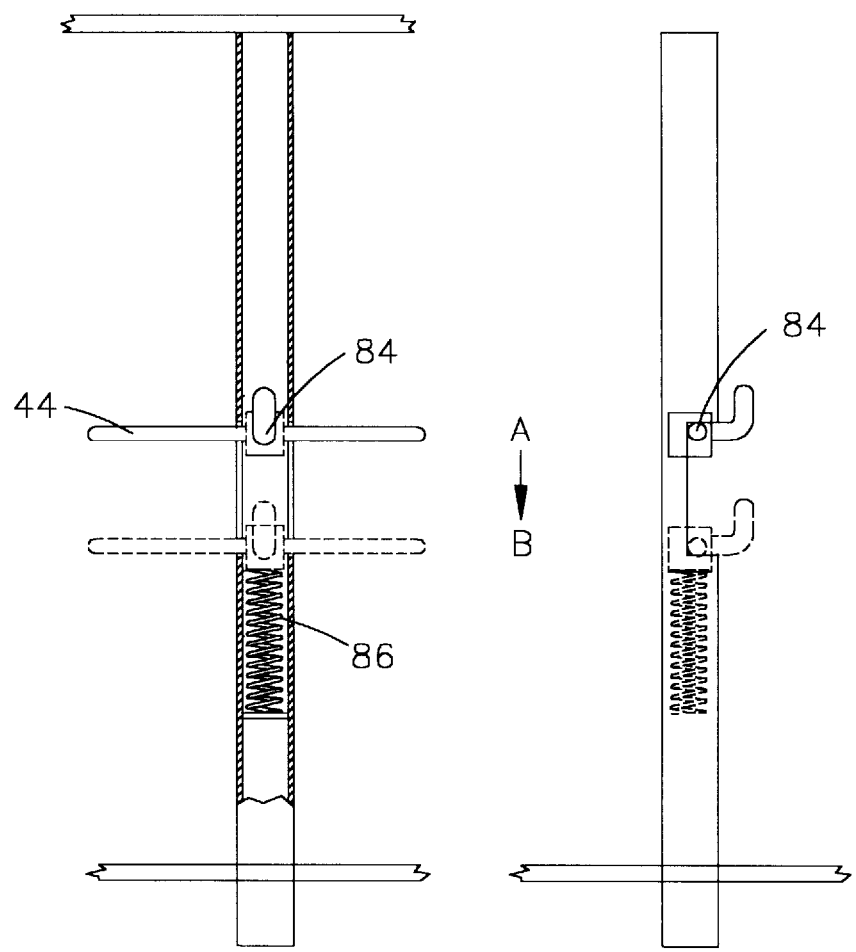
FIG. 6 is a cross-sectional view of a third activation system which can be used in the syringe dispenser system of the present invention.

The sterile mixing chamber 7 can include a syringe needle guide 48, the first sterile septum 24, a polycarbonate block of plastic 50 having passages to connect the syringe needles 22 to a single passage, and a second sterile septum 52. The sterile mixing chamber 7 can also include off the shelf plastic connectors and tubing rather than a solid piece of plastic as shown in FIG. 6 and as described herein below.

The injecting system 9 can include, for example, a Novolin® PenNeedle® 54 which is an off-the-shelf item. The Novolin® PenNeedle® 54 is secured into a lower end of the sterile mixing chamber manifold 7 and penetrates the second septum 54 as it is inserted into the sterile mixing chamber manifold 7.

The sterile sealing cap 11 covers the Novolin® PenNeedle® 54 to keep the syringe needle 22 sterile prior to and after injections. The composition of the sterile sealing cap 11 will be described with respect to FIG. 8.

The protective support 13 structure attaches all the above-mentioned systems and includes a threaded tube shoulder stop 56.

Operation of the device is as follows. Reference will be made to FIGS. 1A, 1B, 2A and 2B with respect to loading the insulin in the syringe reservoir 20 into the portable syringe dispenser system and injecting 5 units of R insulin and 7 units of N insulin, as an example.

To load syringe reservoirs 20 into the portable syringe dispenser system, the portable syringe dispenser system is armed by pulling back on the arming knob 40 until a "click" is heard. This arms a spring activated activation button 46 (FIGS. 1A and 2A) and moves the activation bar 44 from a first position (resting position) to a second position (armed position). The arming knob 40 is then pushed forward to the first position (resting position).

A first syringe (0.5 cc or 1.0 cc) is filled to capacity with an insulin of choice using a conventional procedure for filling the syringe. The syringe is then placed (snapped) into a first syringe holder 58 in the portable syringe dispenser system. The needle 22 of the first syringe passes through the first sterile septum 24 in the sterile mixing chamber 7. The first syringe reservoir 20 is then labeled with the type of insulin in the first syringe. A second syringe is then filled to capacity with a second insulin of choice. The second syringe is then placed into a second syringe holder 58 in the portable syringe dispenser system. The needle 22 of the second syringe passes through the first sterile septum 24 in the sterile mixing chamber 7. The second syringe reservoir 20 is then labeled with the type of insulin in the second syringe. The first and second reservoirs 20 can also be labeled prior to insertion into respective holders.

The Novolin® PenNeedle® 54, or similar syringe needle, is then screwed onto the tip of the syringe dispenser system. The Novolin® PenNeedle® 54 passes through the second sterile septum 52. The sterile mixing chamber 7 is primed by, for example, as shown in FIGS. 1A and 2A, turning the indicator dial 34 provided for each syringe reservoir 20. For example, an indicator dial 34 of the first syringe reservoir 20 is turned until the syringe plunger holder 59 engages the syringe plunger 26 and insulin comes out of the Novolin® PenNeedle® 54. An indicator dial 34 of the second syringe reservoir 20 is turned until the syringe plunger holder 59 engages the syringe plunger 26 and insulin comes out of the Novolin® PenNeedle® 54. The indicator dials 34 can be separate dials or can be on the injection tube shoulder 34 as shown in FIG. 2A. In FIG. 2A, the dosage markings must be along side the threaded rod 28 and the zero position must be aligned with the threaded tube shoulder stop 56. The dosage markings must be the same as those on the syringe.

A first embodiment of the activation system 5 according to the present invention will now be described with respect to FIG. 3. The indicator dials 34 (see FIGS. 1A and 2A) are aligned with the 1 unit markings on each syringe reservoir 20. The activation button 46 is then pushed and the activation bar 44 moves from the second position (armed position) to the first position (resting position) by the force of a spring 60. The movement of the activation bar 44 pushes the threaded tube shoulder 32 (see FIGS. 1A and 2A) of each dose adjusting indicator system 3 to the threaded tube shoulder stop 56. In the first position (resting position), the indicator dials 34 should be aligned with the zero markings on the syringe reservoir 20. If this is not the case, the indicator dials 34 can be adjusted by loosening the zero set screw (FIGS. 1A and 2A) and turning the indicator dials 34 up or down the threaded tube 30 until they are aligned with the zero markings on the syringe reservoir 20. The zero set screw is then retightened, securing the indicator dials 34 to the threaded tube 30. The syringe dispenser system is now ready for injection.

As noted above, insulin reservoirs are loaded by pulling the arming knob 40 until a "click" is heard. This arms the spring activated activation button 46 by pulling back the activation bar 44 from the first position (resting position) to the second position (armed position). The arming knob 40 is then pushed forward to its resting position. A locking mechanism (not shown) remains in place. A first indicator dial 34 on the first syringe reservoir 20 is then rotated to prepare for an injection of 5 units of R insulin. When the first indicator dial 34 is turned the threaded tube 30 also turns so that the threaded tube 30 moves up the threaded rod 28. The first indicator dial 34 moves up and down the first syringe reservoir 20 until the correct units on the first syringe and the first indicator dial 34 are aligned. The first indicator dial 34 on the first syringe reservoir 20 having the R insulin is turned until it is aligned with, for example, the 5 unit mark on the first syringe. The second indicator dial 34 on the second syringe reservoir 20 having the N insulin is then turned so that the second indicator dial 34 is aligned with, for example, the 7 unit mark on the second syringe reservoir 20. It should be noted that more than two syringes can be employed. For simplicity, however, this explanation refers to and the drawings show only two syringes.

The first and second syringes are now set to release the desired amount of insulin. As set forth above, the needle of each syringe is inserted into the sterile septum 52 (the second sterile septum) in the sterile mixing chamber 7. Combining needles 62 are located in the sterile mixing chamber 7 (FIGS. 1A and 2A). The combining needles 62 are, for example, holes drilled through a plastic block 50 used as the sterile mixing chamber 7 as shown in FIGS. 1A and 2A. The combining needles 62 respectively receive the needles from each syringe and are joined in the Novolin® PenNeedle® 54 at the tip of the syringe dispenser system. That is, the combined insulin in each needle is output through the Novolin® PenNeedle® 54. The Novolin® PenNeedle® 54 is then inserted subcutaneously and the activation button 46 is depressed.

Figure 4:
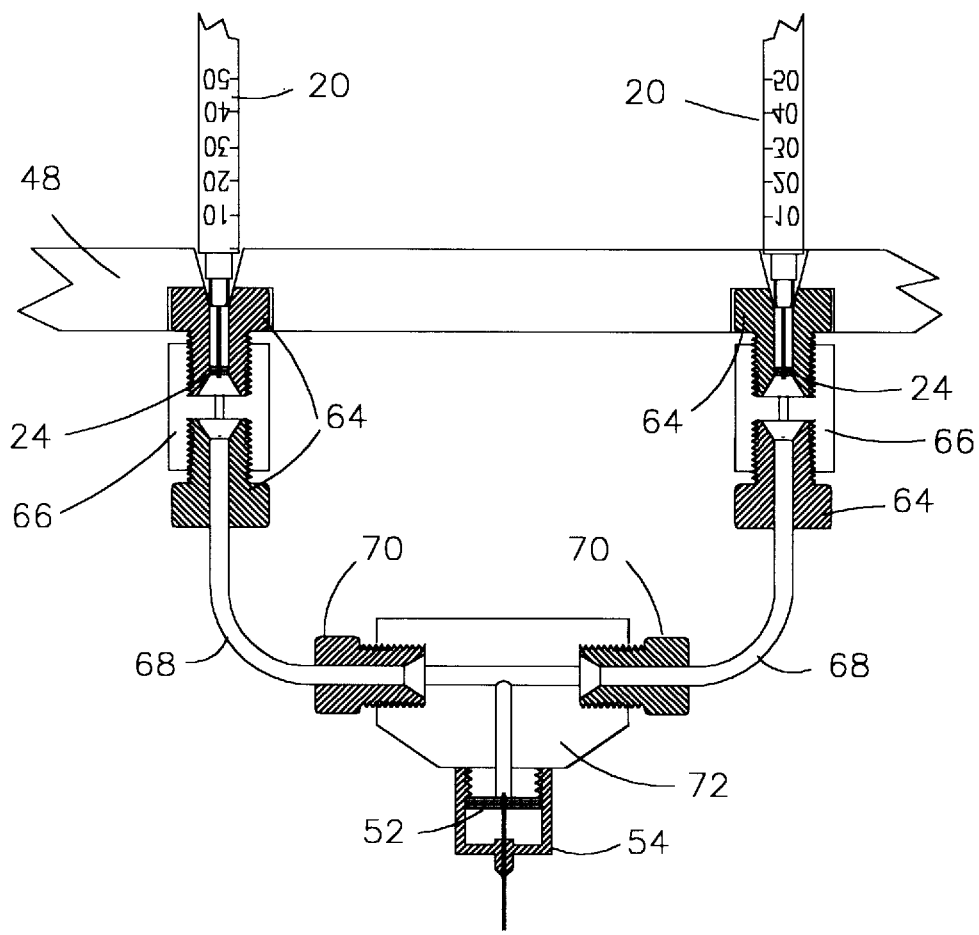
FIG. 4 is a cross-sectional view of a sterile mixing chamber according to the present invention which can be used in place of the sterile mixing chamber in FIGS. 1A–2B.

The sterile mixing chamber 7 in FIG. 4 can be used in place of the sterile mixing chamber 7 in FIGS. 1A and 2A. The sterile mixing chamber 7 in FIG. 4 includes the syringe needle guide 48, ferrule-nuts 64, unions 66, tubing 68, tube connectors 70, and tees 72. The ferrule nuts 64 can be for example, P-330 nuts and ferrules manufactured by Tefzel®. The tees 72 (including crosses) can be, for example, P-722 Cross PEEK manufactured by Tefzel®. The unions 66 can be for example, low pressure unions such as the P-602 manufactured by Tefzel®. The tubing 68 is color coded and can be, for example, tubing 1531 manufactured by PEEK. However, any off the shelf compatible fixtures can be employed.

When the activation button 46 is depressed, the activation bar 44 moves from the second position (armed position) to the first position (resting position) by the force of the spring 60. The movement of the activation bar 44 pushes the threaded tube shoulder 32 from each dose adjusting indicator system 3 to the threaded tube shoulder stop 56, thus returning the indicator dials 34 to the zero position. Since the threaded rod 28 is screwed into the threaded tube 30 it too will move the same distance. Further, since the syringe plunger 26 is secured to the threaded rod 28 it will also travel the same predetermined distance in each of the dose adjusting indicator systems 3. Therefore, the syringe plunger 26 of the dose adjusting indicator system 3 having the indicator dial 34 aligned with the 5 unit marking will be depressed exactly 5 units and the syringe plunger 26 of the dose adjusting indicator system 3 with the indicator dial 34 aligned with the 7 unit marking will be depressed exactly 7 units. When the activation button 46 is depressed the premeasured insulins from both reservoirs are released simultaneously into the sterile mixing chamber 7, are combined in the Novolin® PenNeedle® 54 and are injected simultaneously. Therefore, only one needle is necessary to give the required injection, the dose of the medicine in each of the syringes can be adjusted, and several sequential doses can administered without replacing the syringes.

Figures 3, 5:
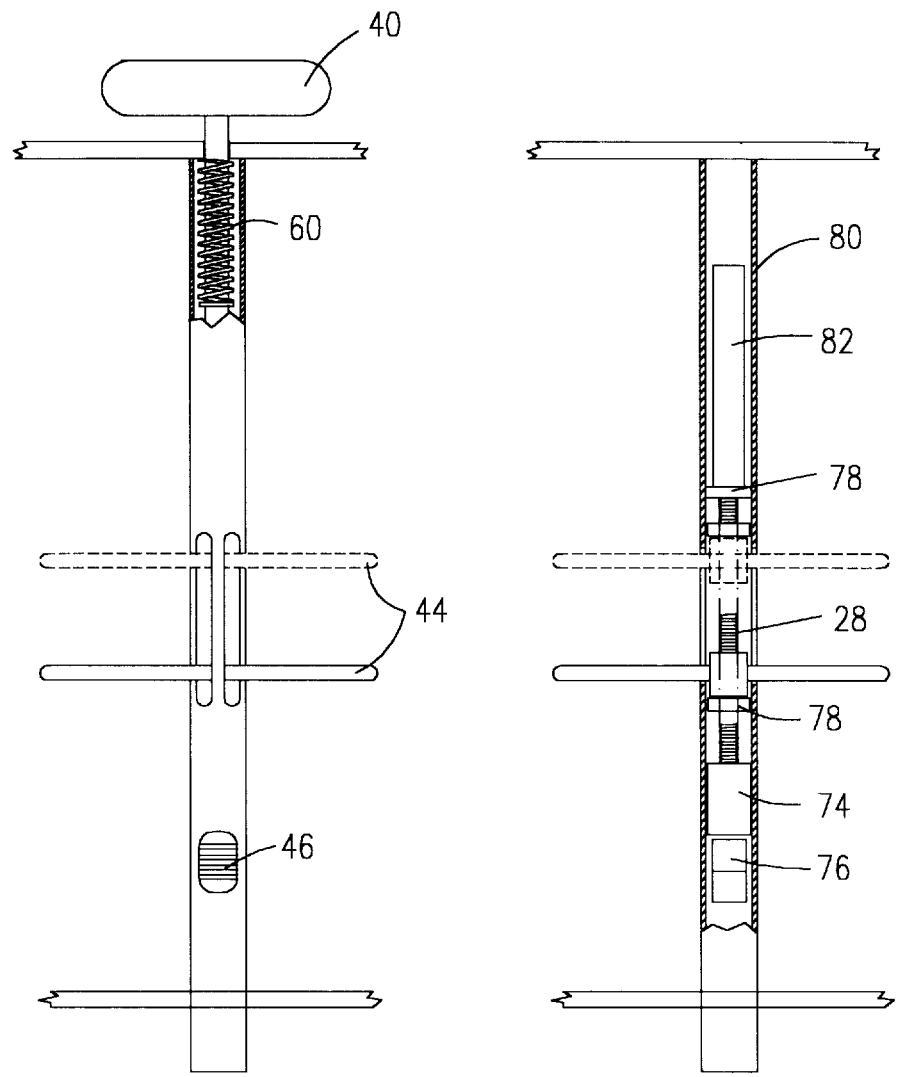
FIG. 3 is a cross-sectional view of a first activation system which can be used in the syringe dispenser system of the present invention.
FIG. 5 is a cross-sectional view of a second activation system which can be used in the syringe dispenser system of the present invention.

FIG. 5 is a cross-sectional view of a second activation system 5 according to the present invention. In FIG. 5, the activation system 5 shown and described in FIG. 3 is replaced by a battery-powered motor 74 which turns the threaded rod 28 enabling the activation bar 44 to travel to the armed position and resting position. A rocker switch 76 for each position starts the motor 74 which activates the activation bar 44. A micro-switch 78 on either end of the threaded rod 28 automatically stops the action of the activation bar 44. An activation system tube 80 houses batteries 82 for the motor 74.

FIG. 6 is a cross-sectional view of a third type of activation system 5 which can be used. This system does not require an activation button 46 to move the activation bar 44. Rather, the activation bar 44 is moved from a resting position A shown in FIG. 6 to an injecting position B by simply pushing a trigger 84. When the trigger 84 is released the activation bar 44 is pushed back to the resting position A by a spring 86. This is the simplest form of the activation system 5.

Figure 7A:
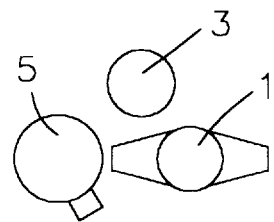
FIGS. 7A–7F are top views of the syringe dispenser system according to the present invention showing the arrangement of various numbers of syringes.
Figure 7D:
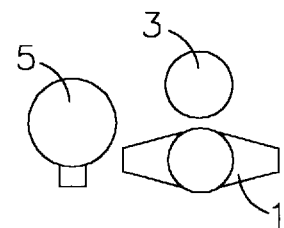
Figure 7B:
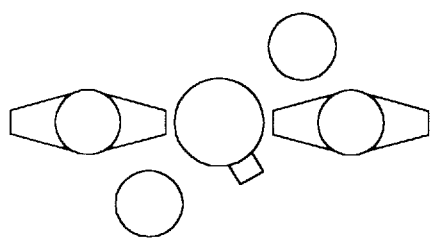
Figure 7E:
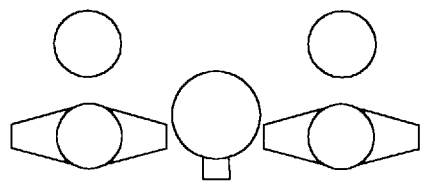
Figure 7C:
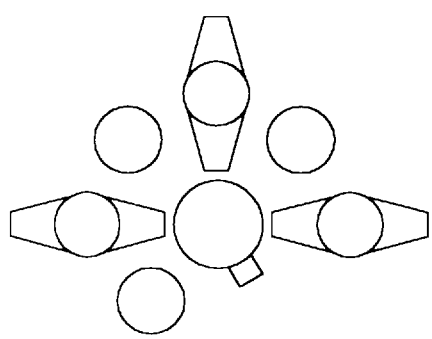
Figure 7F:
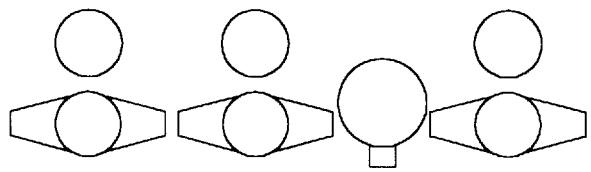

FIGS. 7A–7F show top views of the portable syringe dispenser system and configurations for various numbers of syringes. FIGS. 7A and 7D show a single syringe and include the activation system 5 (button type), dose adjusting indicator system 3 and syringe holder 38. FIGS. 7B and 7E show a multiple syringe system including two syringes. FIGS. 7C and 7F show a multiple syringe system including three syringes. Although only a maximum of three syringes are shown, more than three syringes can be accommodated.

Figure 8:
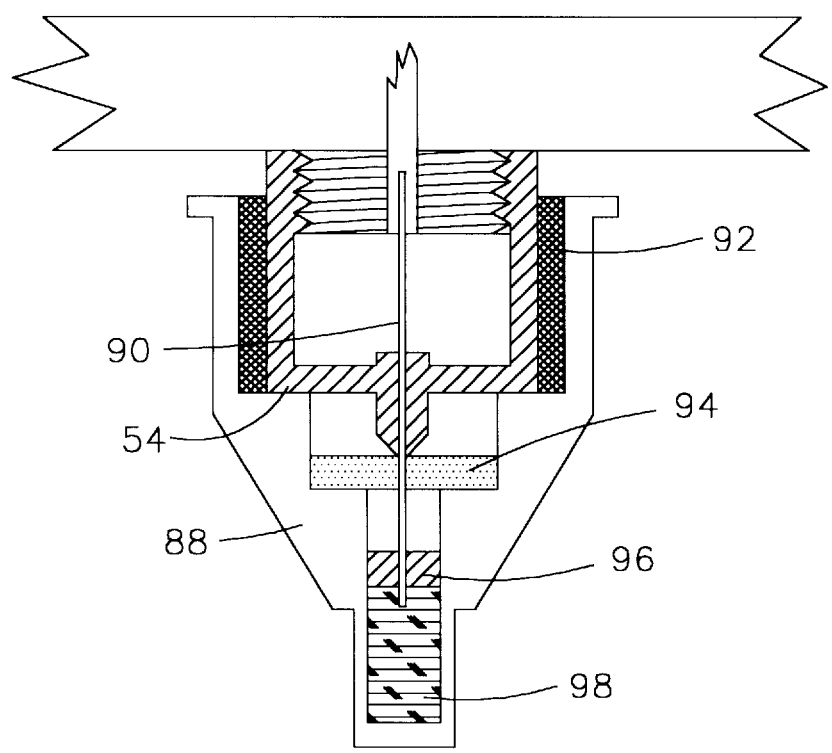
FIG. 8 is an enlarged view of a needle cap used in the syringe dispenser system according to the present invention.

After the injection the Novolin® PenNeedle® 54, or other similar device, can remain on the syringe dispenser system by sealing it with the sterile sealing cap 11 as shown in FIG. 8. The sterile sealing cap 11 includes a plastic holder and guide 88 which receives the syringe tip 90 of the Novolin® PenNeedle® 54. The plastic holder and guide 88 includes a resilient foam liner 92 and a septum 94 (third septum). The syringe tip 90 passes through the septum 94 and into a sterile material 96 such as cotton gauze soaked in alcohol or a similar material. The Novolin® PenNeedle® 54 passes through the sterile material 96 (alcohol soaked gauze) and into a septum rubber 98 rendering it sterile and keeping it sterile for the next injection. If this is unacceptable or the needle has gone through numerous injections, then a new needle can be quickly and easily screwed on. The syringe dispenser system can be stored as is until the next injection. The insulin is kept sterile by storing it between the septums in the sterile mixing chamber 7.

The insulin in each of the syringes can be available for up to 5 days depending on the amount of insulin needed per injection and the type of syringe (0.5 cc or 1.0 cc) used. Each syringe plunger 26 can be seen when the insulin gets low so that one can visually see when the syringe reservoir 20 is empty. When the syringe reservoir 20 is empty then the syringe can be replaced with a new full syringe or the syringe can be refilled and placed back in the reservoir in the syringe dispenser system. The syringe dispenser system remains sterile due to the various septums in the sterile mixing chamber 7.

Resolution of a dosage is as accurate as the markings on the syringe. As noted above, the device is easily calibrated. The size of the syringe dispenser system of the present invention using two syringes is equivalent to that of three syringes together. That is, it is very compact. The more syringes employed, the wider the device becomes but still remains compact compared to carrying separate syringes and fluid medicine such as insulins for each injection.

At approximately one month intervals the sterile mixing chamber hardware needs to be either replaced with new hardware or the old hardware needs to be sterilized and reassembled with new septums.

Figure 9:
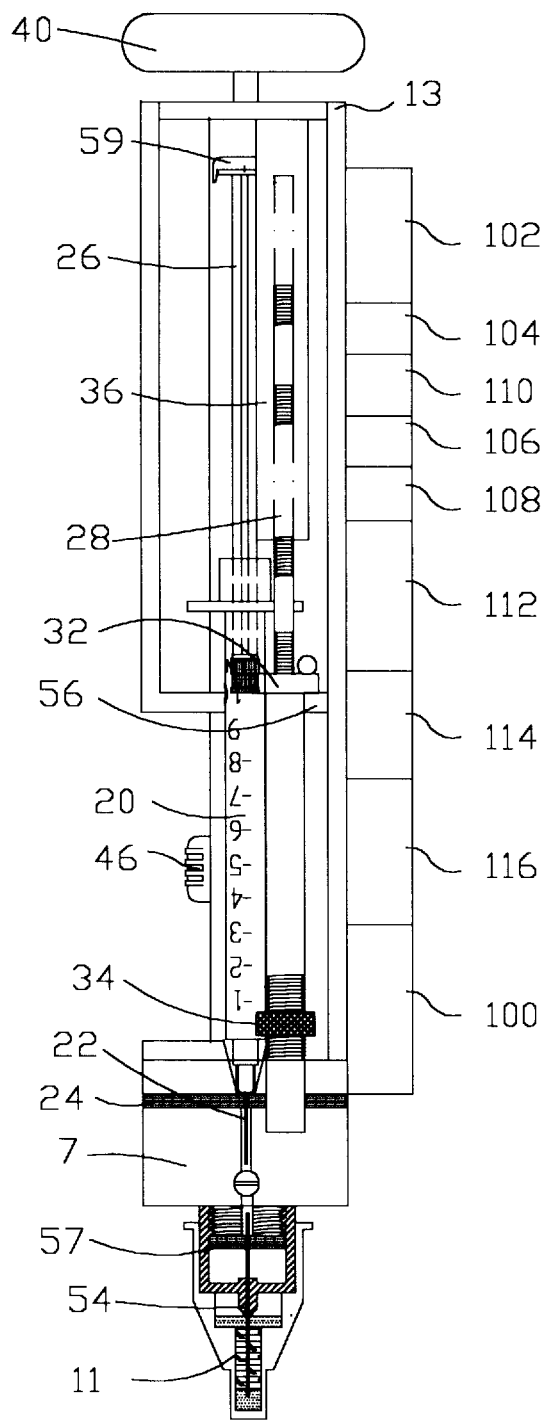
FIG. 9 is a side view of the syringe dispenser system according to a third embodiment of the present invention including a dosage/time recording system.

FIG. 9 is a side view of a syringe dispenser system according to a third embodiment of the present invention including a dosage/time recording system. FIG. 9 is similar to the device shown FIGS. 1A and 1B, however the system also includes a dosage/time recording system attached to a side of the portable syringe dispenser system and having an indicator dial sensor 100, an LCD 102, a clock 104, a set button 106, a memory button 108, a zero button 110, a micro controller having a memory 112, a battery 114 and an RS 232 (or similar) port 116. The operation of the dosage/time recording system shown in FIG. 9 will now be described.

When the activation bar 44 is in the resting position, the indicator dial sensor 100 is zeroed by depressing the zero button 110. A zero(0) is then displayed on the LCD 102. When the activation bar 44 is in the armed position, the indicator dial 34 is free to be dialed to a desired dose. As the indicator dial 34 is turned, the indicator dial sensor 100 detects the position of the dial. This position corresponds to the amount of insulin to be injected. This amount is displayed on the LCD 102. Calibration of the indicator dial sensor 100 and the syringe markings, i.e., turns per indicator dial corresponding to markings on the syringe 42, are made with the set button 106 and are input only once for each syringe. The indicator dial sensor 100 can be, for example, optical, electrical or mechanical, and can be any type that is commercially available. There is one indicator dial sensor 100 for each indicator dial 34. The set button 106, the memory button 108 and the zero button 100 is menu driven by the micro controller 112.

When the desired dose from each syringe is determined in each of the syringes 42, and the injection is completed, the amount of fluid medicine, for example, insulin, from each syringe, in addition to, but not limited to, the time and date, are recorded and stored in the memory of the micro controller 12. A number of recordings can be made to the memory.

The clock 104 determines the time and date and can be set using the set button 106. The stored recordings can be recalled with the use of the memory button 108. The battery 114 runs the clock and the micro controller with memory 112. The RS 232 port 116 is used to download all the stored information. The stored information can be downloaded into a memory or can be sent directly to a doctor by way of, for example, telephone lines.

This embodiment of the present invention provides the advantages of, for example, a diabetic person, using the system of the present invention to not only adjust each individual dose and amount of each type of insulin in a portable, reusable system, but can also allow the person to record vital information relating to each injection with no additional effort on their part. As noted above, this information can be downloaded into available software to be processed or can be sent directly and immediately to a doctor who can instantly evaluate the patient. It is also of great use to correlate the information just obtained with information from recording blood glucose monitors. This information is a powerful tool in making immediate evaluations between, for example, insulin injections and blood sugars, to accurately assess (insulin) therapy.

These features of the present invention provide the advantages that multiple injections of fluid medicine can be performed easily and simultaneously with a compact device that maintains sterility of the fluid medicine and the needles. The syringes and needles can be reused because the device maintains sterility. Therefore, the present invention is a cost effective alternative to using separate syringes and needles for each type of fluid medicine required. The syringe dispenser system of the present invention is also compact and portable so that it can be easily carried and used discretely.

The present invention has been described with respect to the injection of insulin and using two syringes. However, more than two syringes can be used. Further, the present invention is not limited to insulin injections. Rather, any type of fluid medicine can be employed. In addition, a Novolin® PenNeedle® has been described as being used in the present invention. However, any type of needle similar to the PenNeedle® can be employed.

Although a preferred embodiments of the present invention have been shown and described, it will be appreciated by those skilled in the art that changes may be made without departing from the principles and spirit of the invention which is defined in the appended claims and their equivalents.

We claim:

1. A syringe dispenser system, comprising:
    a housing including a plurality of dose adjustable syringe holders therein;
    a plurality of syringes inserted into said plurality of dose adjustable syringe holders, said plurality of syringes each including fluid medicine and capable of several sequential dose injections and each having a needle and plunger attached thereto, said fluid medicine being dispensed simultaneously from each of said plurality of syringes; and
    activation means contacting each of said plurality of syringes, for simultaneously dispensing said fluid medicine from said plurality of syringes.

2. A syringe dispenser system according to claim 1, further comprising:
    adjusting means, coupled to each of said plurality of dose adjustable syringe holders, for adjusting the dosage of fluid medicine in each of said plurality of dose adjustable syringes, said adjusting means including:
        indicator means on one of or both of each of said plurality of dose adjustable syringe holders and said syringes;
        threaded rods, a threaded rod provided for each of said plurality of syringes and coupled to said plungers;
        threaded tubes threaded onto each of said threaded rods, respectively;
        an indicator dial, threaded onto each of said threaded tubes and including:
            calibration means extending through said indicator dial and fastening to each of said threaded tubes, said indicator dial pointing to said indicator means on each of said plurality of dose adjustable syringe holders and said syringes;
        a spring loaded activation bar, located across a middle portion of each of said dose adjustable syringe holders and contacting each of said threaded tubes, for simultaneously releasing said fluid medicine from said plurality of syringes.

3. A syringe dispenser system according to claim 2, wherein said calibration means aligns said indicator dial with said indicator means.

4. A syringe dispenser system according to claim 2, further comprising:
    sterile mixing manifold means having a multiple septum opening for receiving each needle from said plurality of syringes and a single septum opening; and
    a screw-on needle, screwed into said single septum opening of said sterile mixing manifold means, for simultaneously receiving and dispensing said fluid medicine from said sterile mixing manifold means.

5. A syringe dispenser system according to claim 1, wherein said sterile mixing manifold means comprises:
    a first septum into which each needle of said plurality of syringes is inserted;
    a passage for receiving each needle, each passage combining into one combined passage, said combined passage being joined at a portion where said screw-on needle attaches; and
    a second septum into which said screw-on needle passes to connect with said combined passage.

6. A syringe dispenser system according to claim 5, further comprising a needle sealing cap for covering said screw-on needle.

7. A syringe dispenser system according to claim 6, wherein said needle sealing cap has an open end for receiving said screw-on needle and a sealed end, said needle sealing cap further comprises:
    a septum located inside said needle sealing cap near said sealed end; and
    sterilizing means packed inside said needle sealing cap for sterilizing said screw-on needle.

8. A syringe dispenser system according to claim 7, wherein said sterilizing means includes alcohol soaked gauze.

9. A syringe dispenser system according to claim 4, wherein each one of said plurality of syringes contains a different type of fluid medicine.

10. A syringe dispenser system according to claim 9, further comprising:
    a spring loaded activation bar having a large force stored therein, attached to said syringe dispenser system, for arming said syringe dispenser system for an injection;
    an arming knob, coupled to said spring loaded activation bar, for arming said spring loaded activation bar; and
    injection means, coupled to said spring loaded activation bar, for releasing the large force stored in said spring loaded activation bar and simultaneously releasing the fluid medicine in each of said plurality of syringes into said screw-on needle.

11. A syringe dispenser system according to claim 10, wherein said plungers are independently and simultaneously moved when said injection button is pushed.

12. A syringe dispenser system according to claim 9, further comprising:
    a battery within said housing;
    a motor connected to said battery in said housing; and
    a microswitch in each of said plurality of dose adjustable syringe holders, coupled to said motor, said injection means and said activation bar, for simultaneously releasing the fluid medicine in each of said plurality of syringes when a small force is applied to said injection means.

13. A syringe dispenser system according to claim 9, further comprising:
    an injection button, coupled to said spring loaded activation bar, for releasing said spring loaded activation bar and activating said plungers,
    thereby simultaneously dispensing said fluid medicine in said plurality of syringes.

14. A syringe dispenser system, according to claim 2, further comprising a dosage/time recording system.

15. A syringe dispenser system according to claim 14, wherein said dosage/time recording system comprises:
    indicator dial sensor means, coupled to said adjusting means, for detecting a position of said indicator means;
    zeroing means for zeroing said indicator dial sensor means;
    a liquid crystal display (LCD), coupled to said indicator dial sensor means, for displaying an output of said indicator dial sensor means; and
    memory means, coupled to said LCD, for storing information including the amount of fluid medicine injected, date and time.

16. A syringe dispenser system according to claim 15, further comprising:
    clock means, incorporated into said LCD, for determining and outputting the time and date to said memory means; and set means, coupled to said clock means, for setting the time and date of said clock means.

17. A syringe dispenser system according to claim 16, further comprising:

recall means, incorporated into said memory means, for recalling said information stored in said memory means; and downloading means for downloading the recalled information.

18. A syringe dispenser system according to claim 17, wherein said indicator dial sensor means can be one of an optical, electrical and mechanical device.

19. A syringe dispenser system, comprising:

a syringe holding and guiding system including syringes filled with fluid medicine;

a dose adjusting indicator system connected to said syringe holding and guiding system;

an activation system coupled to said dose adjusting indicator system, said activation system including;

an injection button, coupled to said syringes, for simultaneously releasing fluid medicine in each of said syringes; and a spring loaded arming knob, coupled to said injection button, for arming said injection button for an injection; and sterile mixing manifold means, coupled to said syringes, for receiving and simultaneously dispensing said fluid medicine in said syringes.

* * * * *